(12) United States Patent
McPherson et al.

(10) Patent No.: US 6,790,211 B1
(45) Date of Patent: Sep. 14, 2004

(54) ULTRASONICALLY DRIVEN OSTEOTOME HAVING A CURVED TOOL TIP

(75) Inventors: Edward J. McPherson, Manhattan Beach, CA (US); Mark V. Vandewalle, Pierceton, IN (US)

(73) Assignee: Biomet, Inc., Warsaw, IN (US)

( * ) Notice: Subject to any disclaimer, the term of this patent is extended or adjusted under 35 U.S.C. 154(b) by 374 days.

(21) Appl. No.: 10/082,657

(22) Filed: Feb. 25, 2002

(51) Int. Cl.[7] .............................................. A61B 17/56
(52) U.S. Cl. ....................................... 606/84; 606/169
(58) Field of Search .......................... 606/79, 84, 167, 606/169, 99

(56) References Cited

U.S. PATENT DOCUMENTS

| | | |
|---|---|---|
| 5,019,083 A | 5/1991 | Klapper et al. |
| D339,419 S | 9/1993 | Hood et al. |
| D342,313 S | 12/1993 | Hood et al. |
| D344,801 S | 3/1994 | Hughes et al. |
| 5,456,686 A | 10/1995 | Klapper et al. |
| 5,749,877 A | 5/1998 | Young |

*Primary Examiner*—David O. Reop
(74) *Attorney, Agent, or Firm*—Harness, Dickey & Pierce, P.L.C.

(57) ABSTRACT

A tool tip for use with an ultrasonically driven osteotome, is described. The tool tip has a first curvature in a first plane and a second curvature in a second plane oriented ninety degrees from the first plane. The resulting curvature of the tool tip substantially corresponds to the medial curve of a femoral component of a hip replacement system. The tool tip provides easy access to the area in proximity to the medial curve of the femoral component, thus enabling the efficient softening and removal of cement therefrom during revision procedures.

21 Claims, 6 Drawing Sheets

ULTRASONICALLY DRIVEN OSTEOTOME HAVING A CURVED TOOL TIP

FIELD OF THE INVENTION

The present invention relates generally to osteotomes, and more particularly to an ultrasonically driven osteotome including a tool tip having a curvature substantially corresponding to the medial curve of a hip implant.

BACKGROUND OF THE INVENTION

The use of various prosthetic implant systems, such as those used for the total replacement of hips, has become increasingly more commonplace. For example, hip replacements are performed to alleviate conditions caused by osteoarthritis, rheumatoid arthritis, fractures, dislocations, congenital deformities, and other hip-related conditions.

Total hip arthroplasty involves replacing the damaged surfaces of the hip with artificial surfaces. Typically, the surgeon removes the head and neck of the femur 10 and replaces them with a femoral component 12 comprised of a metallic ball 14 and stem 16, as shown in FIG. 1. The femoral component 12 typically has a medial curve portion 18. The stem 16 is usually secured in place with the use of bone cement 20.

Occasionally, various conditions arise with the hip implant, such as the femoral component, and it becomes necessary to perform a revision procedure. As part of the revision procedure, it is sometimes necessary to remove the existing femoral component and replace it with a different femoral component.

The goal in these revision procedures is to remove the existing femoral component and surrounding cement material and preserve the integrity of the normal host tissue. An osteotome is a device which aids the orthopedic surgeon in achieving this goal. Recently, the adaptation of ultrasound technology to develop ultrasonically driven osteotomes that remove cement has made the removal of existing femoral components significantly easier.

The conventional ultrasonically driven osteotome system generally consists of a console to generate ultrasound power, an ultrasonic handpiece, and a variety of tool tips and extenders that are typically controlled by a foot switch during surgery. With the use of a piezoelectric transducer, the console converts electrical energy into mechanical energy. The mechanical energy passes through the tool tip as high frequency energy acoustic waves (20,000 to 100,000 cycles/second or hertz). The energy from the acoustic waves is transferred from the tool tip to the cement, causing intermolecular friction that converts the hard cement into a putty. Minimal heat is generated during this process.

The conventional ultrasonically driven osteotome typically comes with a variety of tool tips to aid in the different aspects of cement removal. Removal of cement is performed using both tactile and audible feedback to ensure host-bone integrity. The ultrasonically driven osteotome is capable of cutting through or perforating host bone, especially in areas of impaired integrity where the bone is thin. An audible high-pitched change in sound, or difficulty in passing the tip through an area, are both indicators that the tool tip is in contact with host bone and should be avoided. The tool tips of the ultrasonic osteotomes are typically manufactured from titanium alloys.

Although most conventional ultrasonically driven osteotomes are suitable for use on the lateral side of the proximal femur, there is significant difficulty accessing the medial side of the proximal femur (i.e., in proximity to the medial curve of the femoral component) due to the configuration of conventional tool tips, which tend to be flat and straight chisel-like members. These conventional tool tips make it especially difficult to remove cement from the area in proximity to the medial curve of the femoral component.

Therefore, there exists a need for a tool tip for an ultrasonically driven osteotome, wherein the tool tip is capable of accessing the area in proximity to the medial curve of a femoral component in order to facilitate cement removal therefrom.

SUMMARY OF THE INVENTION

In accordance with a first embodiment of the present invention, a tool tip for use as an ultrasonically driven osteotome is provided, having a member with a medial surface. The medial surface has a first radius of curvature defined by a first medial surface center point which is medial to the member and a second radius of curvature having a center point defined by a first line lateral to the member. The member further has a lateral surface with a third radius of curvature defined by a third lateral surface center point, medial to said member, and a fourth radius of curvature having a center point defined by a line lateral to said second member. The first and third radius of curvature substantially corresponds to a curve on the surface of an implant component.

In accordance with a second embodiment of the present invention, a tool tip for use as an ultrasonically driven osteotome is provided, comprising: (1) a connection portion for connecting to the osteotome; and (2) an engagement portion having a medial surface with a first radius of curvature defined by a first medial surface center point, which is medial to the member and a second radius of curvature having a center point defined by a first curved line lateral to the member. The member is further defined by a lateral surface with a third radius of curvature formed by a third lateral surface center point medial to the member, and a fourth radius of curvature having a center point defined by a curved line lateral to said second member. The fourth radius of curvature substantially corresponds to a curve on the surface of an implant component.

In accordance with a third embodiment of the present invention, an ultrasonically driven osteotome system is provided, comprising: (1) a driver member; and (2) a tool tip member, comprising: (a) a connection portion for connecting the tool tip member to the driver member; and (b) an engagement portion having a medial surface. With a first radius of curvature defined by a first medial surface center point, which is medial to the member, and a second radius of curvature having a center point defined by a first curved line, lateral to the member. The member further has a lateral surface with a third radius of curvature defined by a third lateral surface center point medial to said member and a fourth radius of curvature having a center point defined by a curved line lateral to said second member. The radius of curvature of the first, third, and fourth radius of curvature substantially corresponds to a curve on the surface of an implant component.

In accordance with a fourth embodiment of the present invention, a method of softening cement adjacent to a femoral component is provided, comprising: (1) providing an ultrasonically driven osteotome system, comprising: (a) a driver member; and (b) a tool tip member, comprising: (i) a connection portion for connecting the tool tip member to the osteotome member; and (ii) an engagement portion having a medial surface with a first radius of curvature defined by a first medial surface center point which is medial to the member and a second radius of curvature having a center point defined by a first line lateral to the member. The member further has a lateral surface with a third radius of curvature defined by a third lateral surface center point medial to the member and a fourth radius of curvature having a center point defined by a line lateral to the member. The third curvature substantially corresponds to a curve on the surface of an implant component; (2) actuating the ultrasonically driven osteotome system so as cause an energy source to be transmitted to the tool tip; and (3) contacting the cement with the tool tip, whereby the energy source causes the cement to soften.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

The same elements or parts throughout the figures are designated by the same reference of characters.

DETAILED DESCRIPTION OF THE PREFERRED EMBODIMENTS

Figure 1:
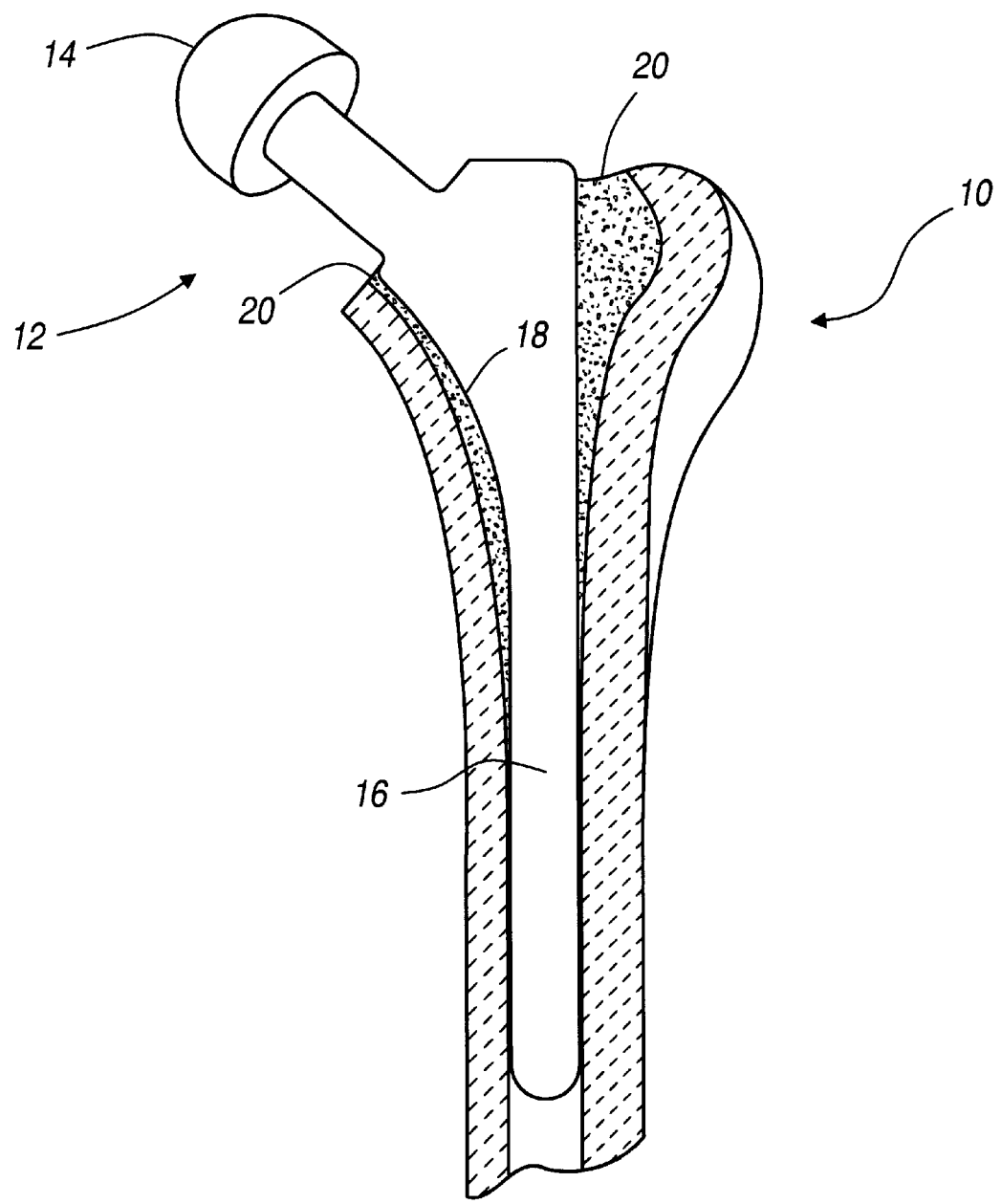
FIG. 1 is an illustration of a partial cross-sectional view of a femoral component implanted into the proximal femur of a patient, in accordance with the prior art.
Figure 2A:
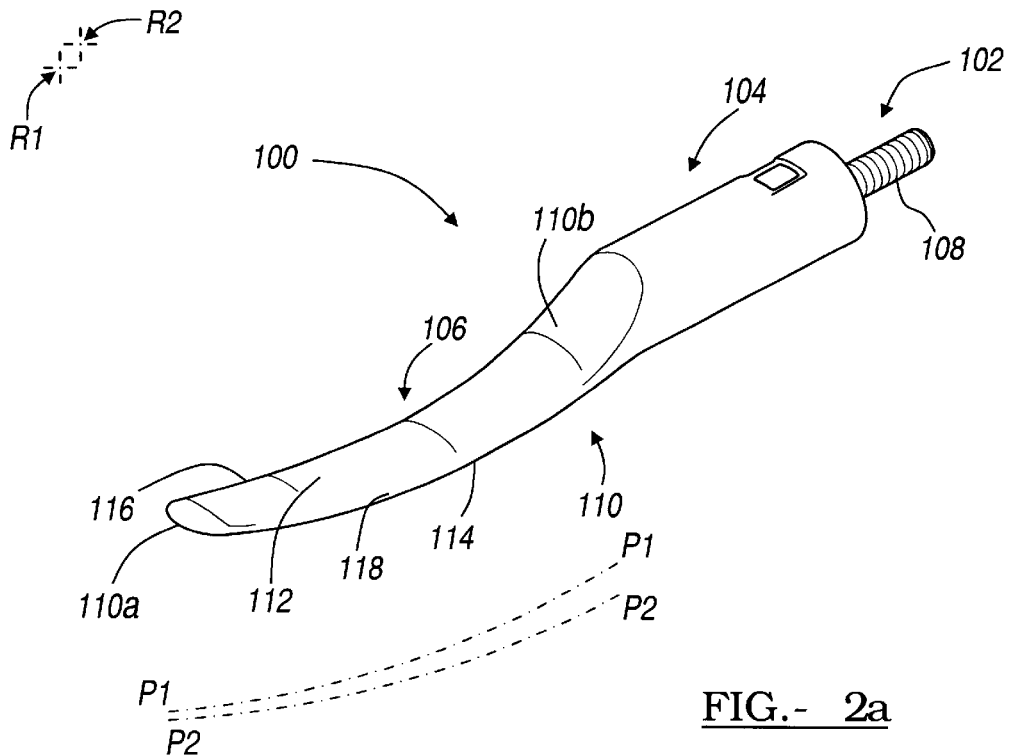
FIGS. 2a and 2b are an illustration of a perspective view of a tool tip, in accordance with the general teachings of the present invention.
Figure 2B:
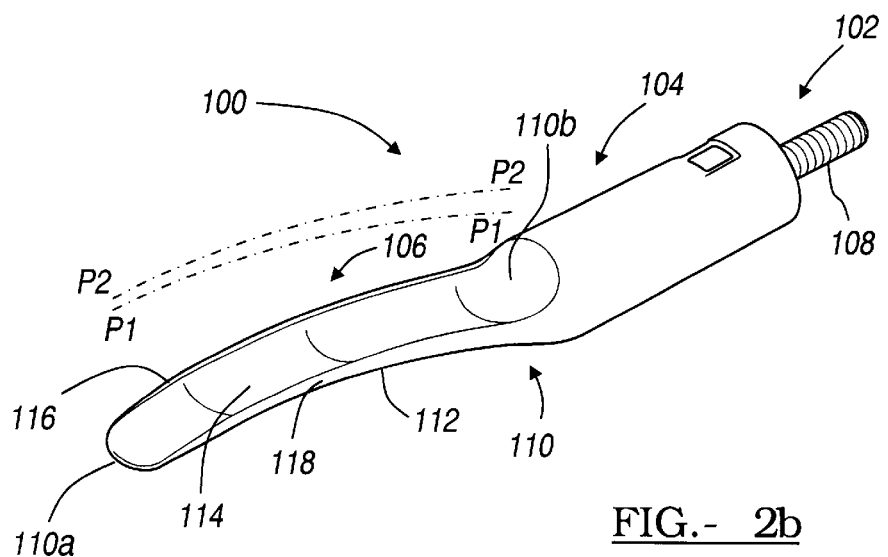

The following description of the preferred embodiment(s) is merely exemplary in nature and is in no way intended to limit the invention, its application, or uses. The spatially oriented descriptions of the components are given only as a mechanism for defining a common coordinate system and are in no way intended to limit the use of the components with a patient. Moreover, while the invention is described using terms such as medial or lateral in conjunction with a femoral implant, it should be understood that these terms can be replaced with first and second when used to describe a tool tip for use with an ultrasonically driven osteotome utilized to remove another class of implants.

Although the following discussion is directed primarily to a tool tip for use with an ultrasonic driver, it should be appreciated that the tool tip could be used with non-ultrasonically driven osteotomes, if so desired.

Referring to FIGS. 2a–5c, there is shown an illustrative tool tip 100 for use with an ultrasonic driver (not shown). The tool tip 100 includes three primary portions: a connection portion 102, a cylindrical portion 104, and an engagement portion 106.

The connection portion 102 is intended to facilitate the connection of the tool tip 100 to the driver (not shown). In this regard, a threaded surface 108 is provided so that the tool tip 100 may simply be screwed into a receptacle on the end of the driver (not shown). It should be appreciated that many other types of connection configurations could be employed as well, including quick-connects, tapers, chucks, and the like. Regardless as to which configuration is employed, the tool tip 100 should be securely held in place to the driver (not shown) so as to prevent inadvertent separation of the tool tip 100 during operation of the driver (not shown).

The cylindrical portion 104 is merely an interface between the connection portion 102 and the engagement portion 106, and also provides a means to grip the tool tip 100.

The engagement portion 106 includes a member 110 that generally has radiuses of curvature defined by two centers of curvature points $R_1$ and $R_2$, and two curved lines $P_1$ and $P_2$ which define a center of curvatures. The member 110 includes an upper or medial surface 112 and a lower or lateral surface 114, as well as side surfaces 116 and 118, respectively. The member 110 preferably has a curvature that substantially corresponds to the medial curve 18 of the femoral component 12 so as to facilitate the removal of cement in proximity to the medial curve 18 of the femoral component 12.

Figure 3:
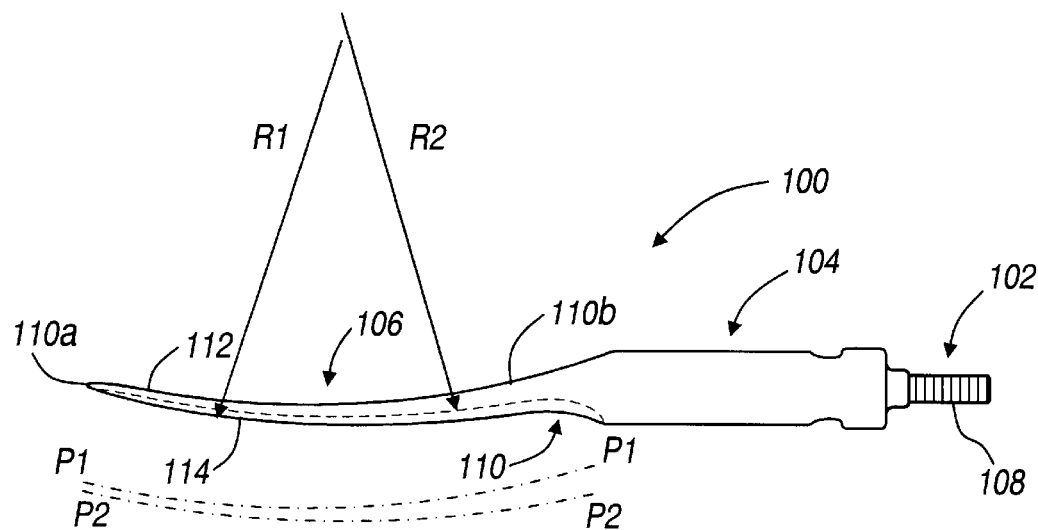
FIG. 3 is an illustration of a partial cross-sectional view of a tool tip, in accordance with the general teachings of the present invention.
Figure 4:
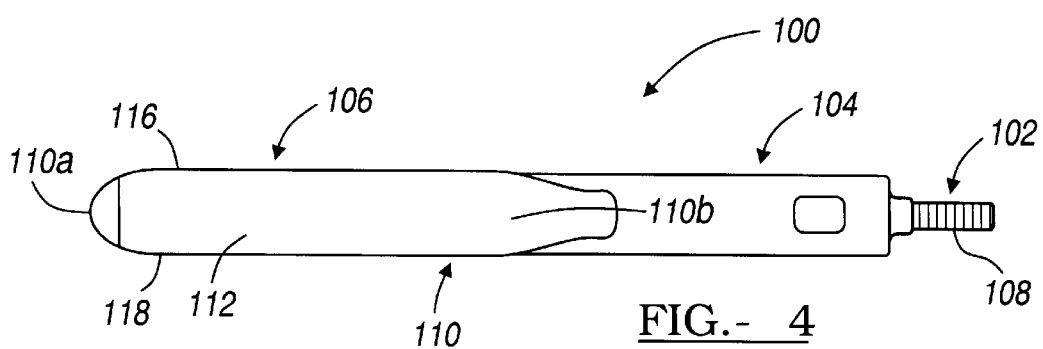
FIG. 4 is an illustration of a top plan view of a tool tip, in accordance with the general teachings of the present invention.

As best seen in FIG. 3, the medial and lateral surfaces 112 and 114 are further defined by a curvature, which utilizes the curved lines $P_1$ and $P_2$ as the centers of curvature. While it is preferred the lines $P_1$ and $P_2$ are positioned medial of the member, line $P_1$ can also be placed on the medial surface 112 so as to define an essentially planar region. It is preferred that the lines $P_1$ and $P_2$ are parallel to and generally conform to the lateral and medial curvature defined by center points $R_1$ and $R_2$. In doing so, the radius of curvature for the surfaces will remain substantially constant over the entire length of the member.

Figure 5:
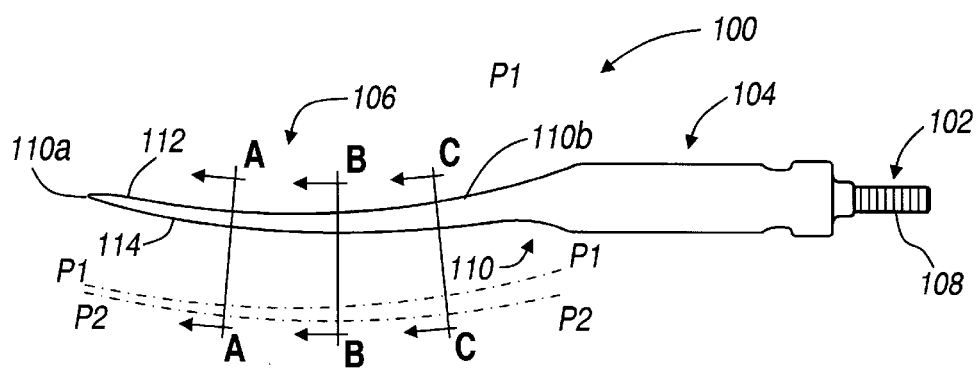
FIG. 5 is an illustration of a side elevational view of a tool tip, in accordance with the general teachings of the present invention.
Figure 5A:
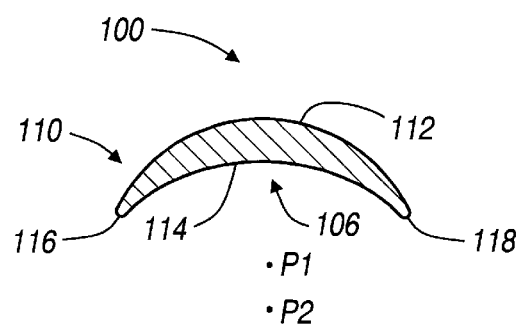
FIG. 5a is an illustration of a sectional view taken along line A—A of FIG. 5, in accordance with the general teachings of the present invention.
Figure 5B:
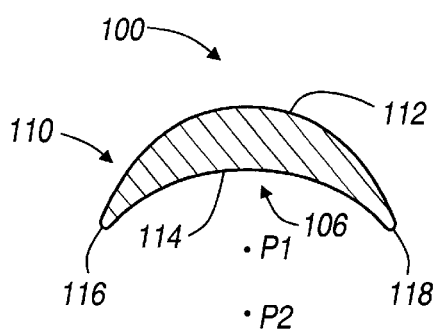
FIG. 5b is an illustration of a sectional view taken along line B—B of FIG. 5, in accordance with the general teachings of the present invention.
Figure 5C:
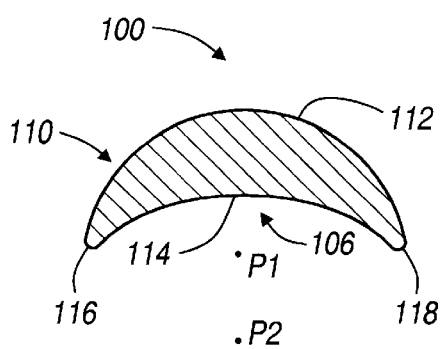
FIG. 5c is an illustration of a sectional view taken along line C—C of FIG. 5, in accordance with the general teachings of the present invention.

It is envisioned, however, that the lines $P_1$ and $P_2$, which are parallel to their respective surfaces 112 and 114, could vary in trajectory, thus producing a varying radius of curvature for the surfaces over the length of the tool tip 100. As best seen in FIGS. 5a–5c, the radius of curvature of the surfaces 112 and 114 with respect to $P_1$ and $P_2$ are substantially constant. The thickness of member 110, which increases from the front portion 110a of the member 110 to the rear portion 110b, is best characterized by the change in distance between the two lines $P_1$ and $P_2$.

The lateral surface 114 is concave and preferably is defined in one plane by the line $P_2$ which correlates to a second radius of curvature on the surface of the implant device, thus allowing the member 110 to be positioned close to the implant. The lateral surface 114 further defines a convex shape in a second plane which is oriented 90° with respect to the first plane and generally corresponds to a medial curve of the implant.

The medial surface 112 has a convex surface with a curvature center point corresponding to the line $P_1$. The medial surface 112 is further concave in a second plane which is 90° to the first plane. The convex medial surface 112 is designed so as to minimize the interaction of the member 110 with the natural bone material.

As FIGS. 5a–5c illustrate, the radius of the member 110 remains substantially constant from one end from the front portion 110a of the member 110 to the rear portion 110b of the member 110. In the embodiment shown, only the thickness of the member 110 changes. By gradually decreasing the thickness of the member 110 as it approaches the front portion or the distal tip 110a, the tool tip 100 is able to penetrate very tight spaces. The lateral surface 112 has a curvature defined by a lateral surface center of curvature $R_1$. The medial surface 114 also has a first curvature defined by a medial surface center of curvature $R_2$.

Figure 6:
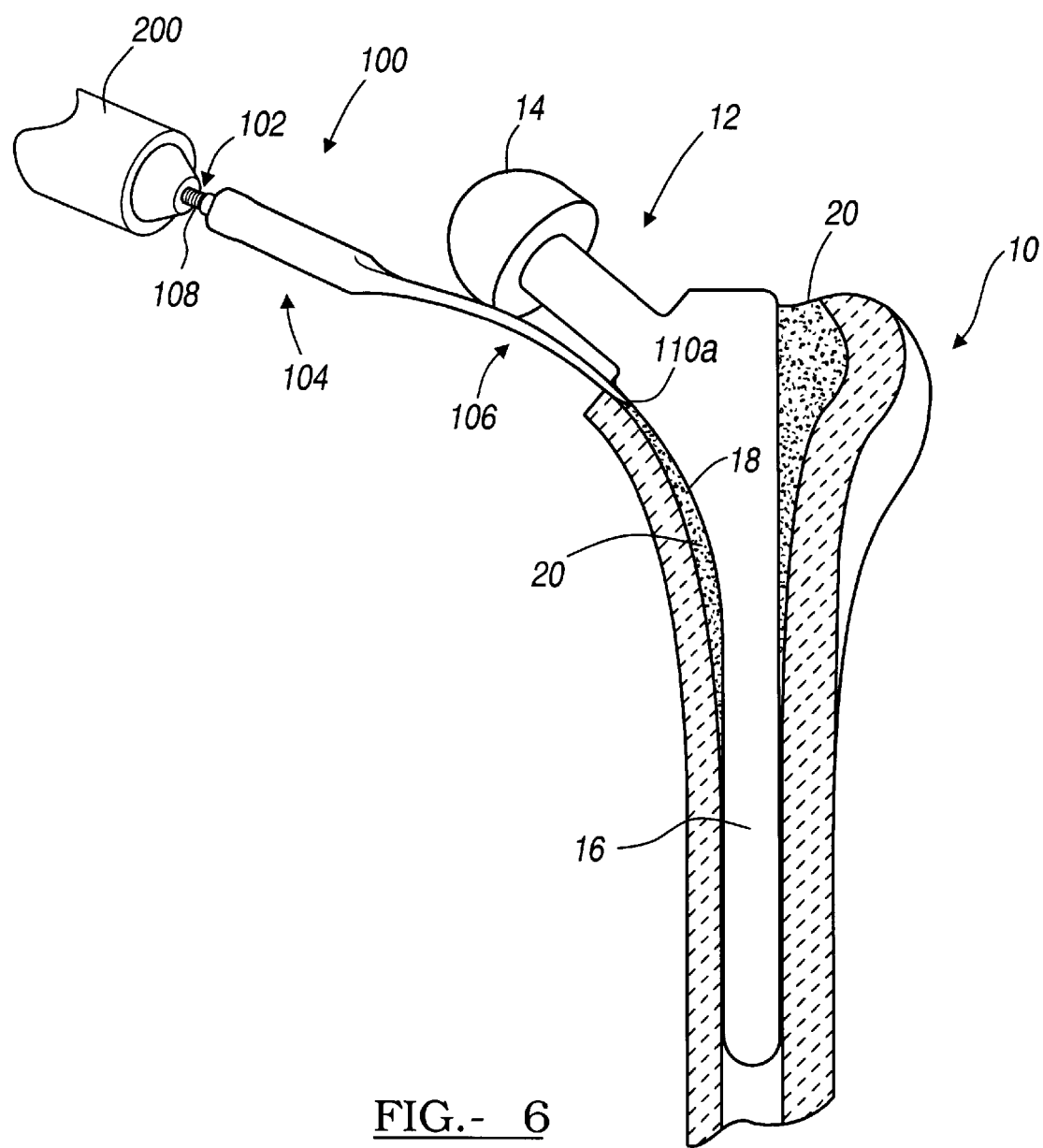
FIG. 6 is an illustration of a partial cross-sectional view of an tool tip engaging the area in proximity to the medial curve of a femoral component in order to facilitate cement removal therefrom, in accordance with the general teachings of the present invention.
Figure 7:
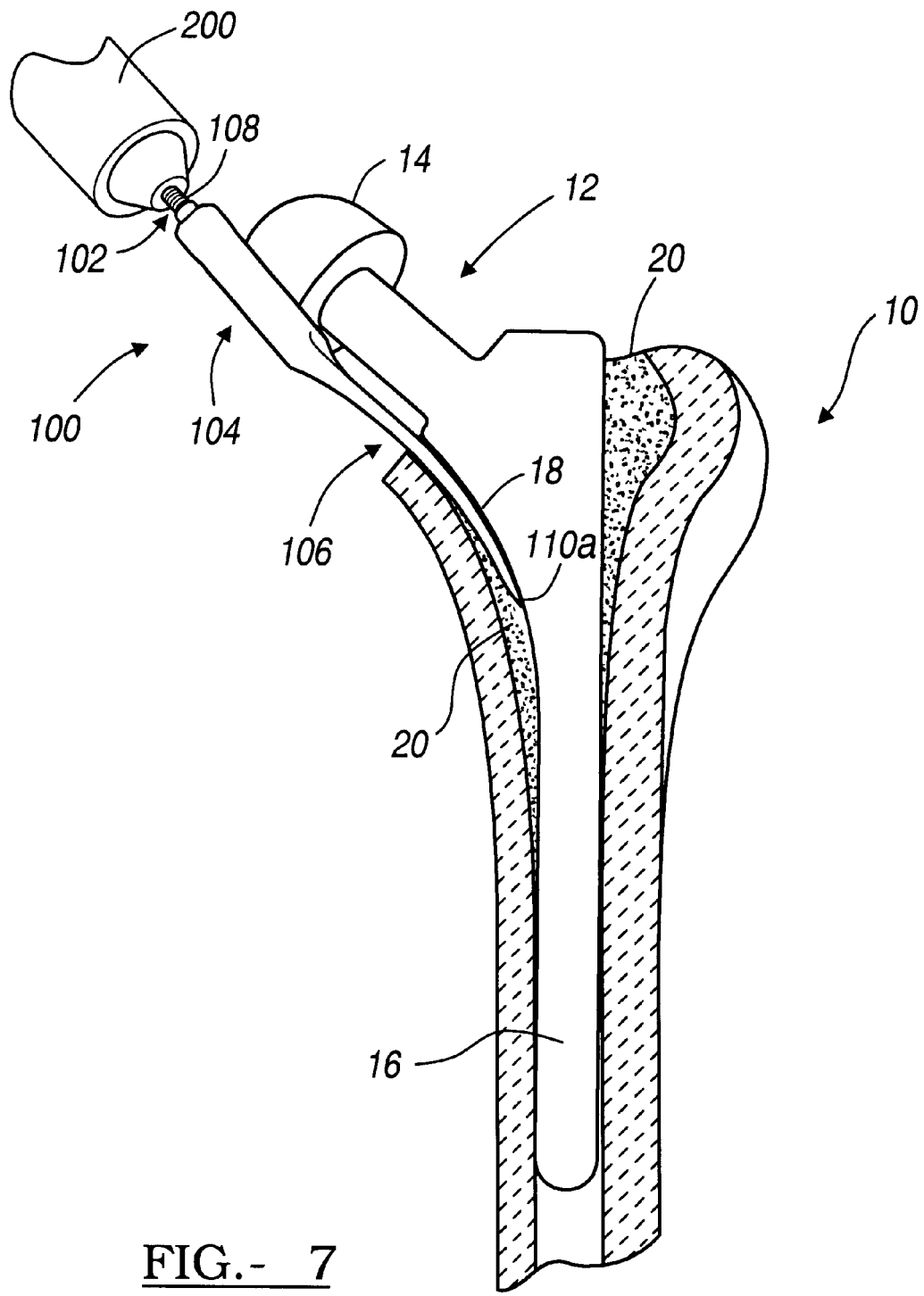
FIG. 7 is an illustration of a partial cross-sectional view of an tool tip further engaging the area in proximity to the medial curve of a femoral component in order to facilitate cement removal therefrom, in accordance with the general teachings of the present invention.

An illustrative method of using the tool tip 100 in conjunction with an ultrasonic driver 200 will be described with reference to FIGS. 6–7. Although the following discussion is primarily directed to facilitating removal of cement adjacent to the medial curve 18 of the femoral component 12, the tool tip 100 of the present invention is equally adapt at facilitating removal of cement from the lateral side of the femoral component 12.

Initially, the tool tip 100 is secured to the driver 200 by the connection portion 102. The driver 200 is then actuated in accordance with conventional practice, causing the acoustic energy to flow through the tool tip 100. The surgeon will at this point begin to gain access to the area of the femur 10 in proximity to the medial curve 18 of the femoral component 12. Because the front portion 110a has a reduced thickness, and because the member 110 of the tool tip 100 is curved as described, the front portion 110a easily penetrates the area in proximity to the medial curve 18 of the femoral component 12. Because the member 110 has substantially the same curvature as the medial curve 18, the tool tip 100 should be able to avoid unintentionally contacting any bone tissue. As the cement 20 is softened, the surgeon can then insert the front portion 110a further into the cavity so as soften deeper deposits of cement 20 so as to facilitate removal of the femoral component 12. Once a sufficient amount of cement 20 has been softened, the femoral component 12 is then removed from the femur 10.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. A tool tip for use as an ultrasonically driven osteotome to remove an implant component, comprising:
   a member having a medial surface with a first radius of curvature defined by a first medial of curvature point which is medial to said member, and a second medial radius of curvature having a center of curvature defined by a first line, and a lateral surface with a third radius of curvature defined by a third lateral of curvature point which is medial to said member and a fourth lateral radius of curvature having a center of curvature defined by a second line lateral to said member, wherein said third radius of curvature substantially corresponds to a first curved surface on the implant component.

2. The invention of claim 1 wherein said first line is substantially parallel to said medial surface.

3. The invention of claim 1 wherein said second line is substantially parallel to said lateral surface.

4. The invention of claim 1 wherein said fourth radius of curvature generally corresponds to a second curved surface on the implant component.

5. The invention of claim 1 wherein said lateral surface is convex in a first plane and concave in a second plane oriented about 90° with respect to said first plane.

6. The invention according to claim 1 further comprising a connection portion formed on a surface of the tool tip.

7. The invention according to claim 1 wherein the first line is lateral to said member.

8. The invention according to claim 6 wherein the connection portion has a threaded surface formed thereon.

9. The invention according to claim 1 wherein said first radius is along the length of the member.

10. The invention according to claim 1 wherein the member has a substantially decreasing thickness along the length of the member.

11. The invention according to claim 1 wherein the member has proximal portion and a distal portion, wherein the distal portion has a smaller thickness than the proximal portion.

12. A tool tip for use as an ultrasonically driven osteotome, comprising:
    a connection portion for connecting to the osteotome; and
    an engagement portion having a medial surface with a first radius of curvature defined by a first medial surface center of curvature point which is medial to said member and a second radius of curvature having a center of curvature defined by a first curved line lateral to said member, and a lateral surface with a third radius of curvature defined by a third lateral surface center of curvature point medial to said member and a fourth radius of curvature having a center of curvature defined by a second curved line lateral to said second member, wherein the fourth radius substantially corresponds to a curve on the surface of an implant component.

13. The invention of claim 12 wherein said first line is substantially parallel to said medial surface.

14. The invention of claim 12 wherein said second line is substantially parallel to said lateral surface.

15. The invention of claim 12 wherein said fourth radius of curvature generally corresponds to a second curved surface on an implant component.

16. The invention of claim 12 wherein said lateral surface is convex in a first plane and concave in a second plane oriented about 90° with respect to said first plane.

17. The invention according to claim 16 wherein the connection portion has a threaded surface formed thereon.

18. The invention according to claim 16 wherein said second radius is substantially constant along the length of the member.

19. The invention according to claim 16 wherein the member has a substantially decreasing thickness along the length of the member.

20. The invention according to claim 16 wherein the member has proximal portion and a distal portion, wherein the distal portion has a smaller thickness than the proximal portion.

21. A method of softening cement adjacent to a femoral component, comprising:
providing an ultrasonically driven osteotome system, comprising:
a driver member; and
a tool tip member, comprising:
a connection portion for connecting the tool tip member to the driver member; and
an engagement portion having a medial surface with a first radius of curvature defined by a first medial surface center of curvature point which is medial to said tool tip member, and a second radius of curvature defined by a first curved line lateral to said tool tip member and a lateral surface with a third radius of curvature defined by a third lateral surface center of curvature point medial to said tool tip member and a fourth radius of curvature having a center of curvature defined by a second line lateral to said second tool tip member, wherein the second curvature substantially corresponds to a first curve on the surface of an implant component;
actuating the ultrasonically driven osteotome system so as cause an energy source to be transmitted to the tool tip; and
contacting the cement with the tool tip, whereby the energy source causes the cement to soften.

* * * * *

UNITED STATES PATENT AND TRADEMARK OFFICE
CERTIFICATE OF CORRECTION

PATENT NO. : 6,790,211 B1
DATED : September 14, 2004
INVENTOR(S) : McPherson et al.

It is certified that error appears in the above-identified patent and that said Letters Patent is hereby corrected as shown below:

<u>Column 3,</u>
Line 12, after "as" insert -- to --.
Lines 52 and 57, "an" should be -- a --.

<u>Column 6,</u>
Line 34, "an engagement portion" should be -- a member --.
Line 43, delete second occurrence of "second".

<u>Column 8,</u>
Line 4, delete "second".
Line 10, after "as" insert -- to --.

Signed and Sealed this

Fourth Day of January, 2005

JON W. DUDAS
*Director of the United States Patent and Trademark Office*